United States Patent [19]
Seki et al.

[11] 3,984,189
[45] Oct. 5, 1976

[54] METHOD AND APPARATUS FOR DETECTING DEFECTS IN A SURFACE REGARDLESS OF SURFACE FINISH

[75] Inventors: Takeo Seki, Kokubunji; Itsuji Maeda, Akishima, both of Japan

[73] Assignees: Hitachi Electronics, Ltd.; Nisshin Steel Co., both of Japan

[22] Filed: Dec. 2, 1974

[21] Appl. No.: 528,847

Related U.S. Application Data

[63] Continuation-in-part of Ser. No. 325,055, Jan. 19, 1973, abandoned.

[52] U.S. Cl. ............................. 356/73; 250/563; 356/200; 356/209; 356/210; 356/237
[51] Int. Cl.² ................. G01N 21/00; G01N 21/16
[58] Field of Search ............ 356/199, 200, 209, 210, 356/211, 212, 73, 237; 250/563, 572

[56] References Cited
UNITED STATES PATENTS

| | | | |
|---|---|---|---|
| 2,315,282 | 3/1943 | Snow | 356/210 |
| 3,176,306 | 3/1965 | Burns | 356/200 |
| 3,574,469 | 4/1971 | Emerson | 356/200 |
| 3,591,291 | 7/1971 | Greer, et al. | 356/209 |
| 3,667,846 | 6/1972 | Nater et al. | 250/572 |
| 3,834,822 | 9/1974 | Stapleton et al. | 356/200 |

FOREIGN PATENTS OR APPLICATIONS

| | | | |
|---|---|---|---|
| 894,570 | 4/1962 | United Kingdom | 356/200 |

*Primary Examiner*—Vincent P. McGraw
*Attorney, Agent, or Firm*—Craig & Antonelli

[57] ABSTRACT

A method and apparatus for detecting a flaw, color shading, or the like on the surface of a running object and for producing an electrical signal in response thereto by optically scanning such surface, characterized in that there is provided not only a photoelectric element for receiving the component of light regularly reflected from the surface of the running object, but also means for receiving the component of light irregularly reflected from the surface thereof, thereby to detect all of the defects that may exist on the surface of such object regardless of the surface finish.

28 Claims, 5 Drawing Figures

METHOD AND APPARATUS FOR DETECTING DEFECTS IN A SURFACE REGARDLESS OF SURFACE FINISH

BACKGROUND OF THE INVENTION

CROSS REFERENCE TO RELATED APPLICATION

This application is a continuation-in-part of application Ser. No. 325,055, filed on Jan. 19, 1973, now abandoned.

FIELD OF THE INVENTION

This invention relates to a method and an apparatus for automatically detecting by optical means flaws, color shading, and the like on the surface of metal plates, plastic boards, and the like which may occur during the manufacturing processes thereof.

DESCRIPTION OF THE PRIOR ART

A well-known conventional device for detecting the defects on the surface of metal by flying spot scanning is so constructed that the surface of a running object is scanned in the transverse direction with a beam from a spot light source through a rotary mirror or vibrating mirror, and the light beam reflected from the mirror, after being again reflected on a cylindrical concave mirror, is converged and converted into an electrical signal by means of a photoelectric element for the purpose of detection of the flaws in the running surface. In such a device, if the object is a mirror-polished lustrous one, the light beam is reflected thereon regularly and converged at a point thereby to detect in the form of variations in quantity of regularly reflected light any defects that might exist on the surface of the running object.

On the other hand, if the surface of the running object is grind-finished in the form of hair lines or has a dull finish, the reflected light does not converge a single point, but is scattered over a certain area. Further, in such a case, a considerable texture signal is produced in the device for receiving the regularly reflected light. As a result, the disadvantage of such a device is that defects that may exist on the surface of the running object may not be detected by the regularly reflected light receiver because of the presence of the texture signal, depending on the nature of the defects.

SUMMARY OF THE INVENTION

Accordingly, it is an object of the present invention to provide a method of and apparatus for detecting with high sensitivity all the defects that may exist on the surface of an object regardless of whether such surface is mirror-polished or dull.

DESCRIPTION OF THE PREFERRED EMBODIMENT

Figure 1:
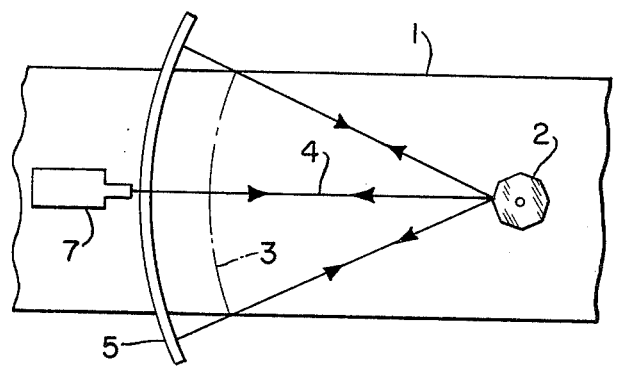
FIG. 1 is a schematic diagram showing a plan view of an embodiment of the present invention.
Figure 2:
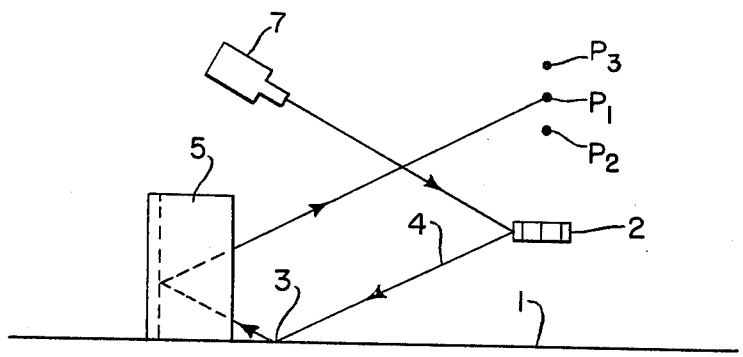
FIG. 2 is a side view of the embodiment of FIG. 1.

Referring to the drawings, in FIGS. 1 and 2 reference numeral 1 designates the surface of an object running at a predetermined speed and numeral 2 designates a polyhedral rotary mirror the axis of which is positioned perpendicular to the surface of the running object so as to scan it in the transverse direction by means of a light beam from the spot light source 7. Numeral 3 designates a scanned locus and numeral 4 designates the scanning light beam reflected on the surface of the running object 1 which is applied to a cylindrical concave mirror 5 having its rotational axis positioned perpendicular to the surface of the running object and in coincidence with the central axis of the same mirror 5, so that light beam 4 reflected from a mirror surface will return to point $P_1$ on the central axis of the polyhedral rotary mirror 2.

As will be understood from the device illustrates in FIGS. 1 and 2 of the drawings, if the running object is lustrous, i.e., has a mirror finish, the entire light beam reflected after the scanning operation will converge at point $P_1$, and therefore, it is possible to detect in the form of current the light beam reflected on the surface of the object by means of a photoelectric element positioned at point $P_1$. In this way, any defects on the surface of the object are detected in the form of variations in detected current as the result of variations in the reflection factor of the surface and reflection angle.

Further, according to the present invention, provision of one or a plurality of photoelectric elements at such points as $P_2$ and $P_3$ at some distance from $P_1$ permits the reception of scattered light due to changes in texture or irregularities on the surface of the object, and thereby makes it possible to detect flaws which otherwise would be hard to detect only with regularly reflected light. This advantage is further emphasized in the case of objects having hairline finish or other types of dull surfaces. In other words, since a significant amount of light reflected from a dull surface of an object will be scattered over a wide area without being converged at point $P_1$ in spite of the cylindrical concave mirror 5, the provision of a photoelectric element only at point $P_1$ will not detect sufficient variations in the amount of light to indicate the presence of flaws because a considerable texture signal is produced due to the quality of the surface of the object, thereby to reduce the detecting sensitivity.

By providing additional independent photoelectric elements at points $P_2$, $P_3$ and so forth to receive the irregularly reflected light, it is possible to collect a relatively large amount of light reflected from various defects which otherwise would be hard to detect with means for reception of only regularly-reflected light; whereas, scattered light due to the irregularities of the surface is collected in a relatively small amount, resulting in a wide variety of defects being detected.

Explanation will be made here of an exemplary method and circuit for processing a signal for flaw detection according to the present invention with reference to FIGS. 3, 4, and 5.

Figure 3:
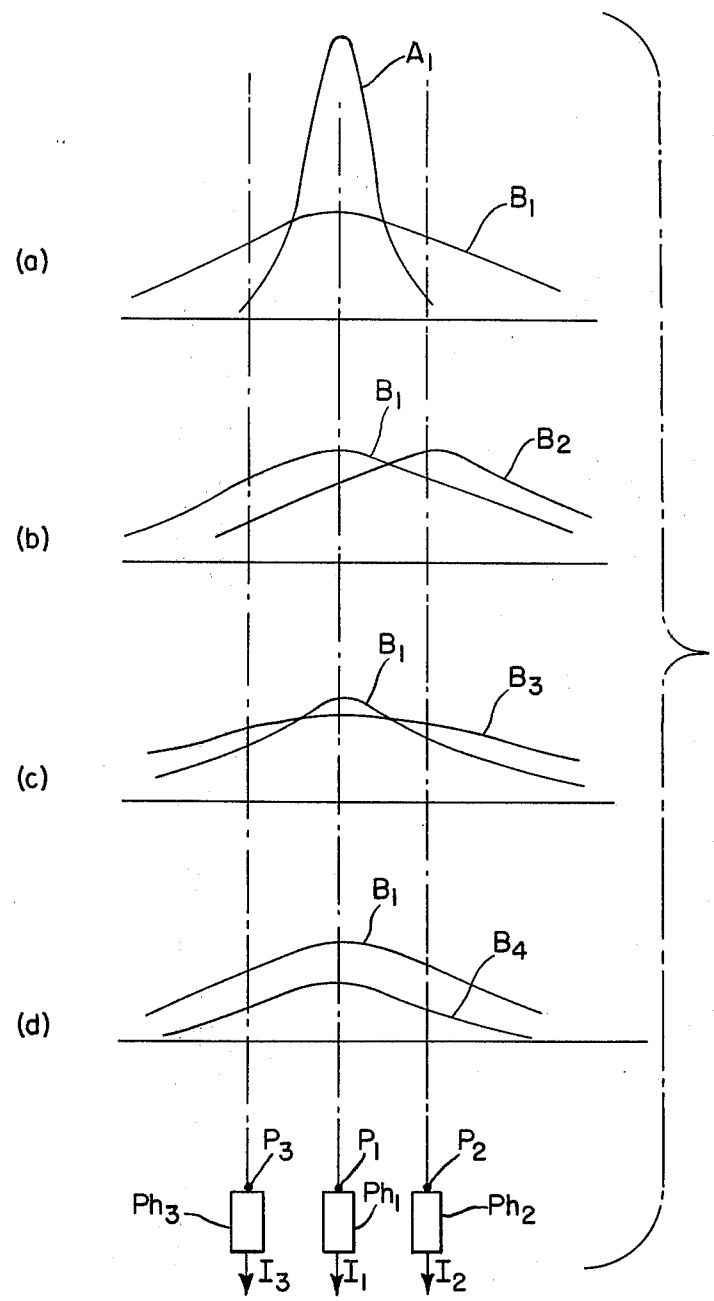
FIG. 3 is a diagram showing the distribution of light reflected and received in the presence of various types of defects for various types of finished surfaces of an object to be inspected.

The distribution of light reflected on various types of surfaces to be inspected is shown in FIG. 3. Symbol $A_1$ of diagram (a) of FIG. 3 shows the distribution of light reflected normally on a mirror-finished surface, while symbol $B_1$ illustrates the distribution of light reflected normally on a dull surface, such as a dull hair-line finished surface. The shadowed areas under curves $A_1$ and $B_1$ represent the total quantity of reflected light which are shown to be equal to each other, the small absorption of light in the inspected surface being neglected to simplify the description. As will be seen, the light reflected on the dull finished surface, even if normal, is scattered so that the light-receiving level is not only low but varies continuously from one detecting position to the next, with the result that variations in the output current of a regularly-reflected light receiving element do not provide an exclusively effective means for flaw detection.

In order to obviate such a disadvantage, if a plurality of irregularly-reflected light receiving elements $Ph_2$, $Ph_3$, ... are provided at points $P_2$, $P_3$, ..., shown in FIG. 2, a more accurate measure of the total amount of reflected light can be obtained in conjunction with the measure of reflected light at point $P_1$. By combining the light levels detected at the various detecting points, smaller variations in the current output of the light detecting system result from variations in the quality of the surface to be inspected, thus making it easier to detect any variations in output level due to a flaw.

Referring to diagram (b) of FIG. 3, showing the displacement of the reflected light due to the shape of defects, the peak of the reflected light $B_1$, which would normally be received at point $P_1$, is transferred to the neighborhood of point $P_2$. The shifting of the point of receipt of the light reflected from the defect occurs due to the shape of the defect which causes a change in the angle of reflection of the light so as to transfer the reflected light $B_2$ from the receiving point $P_1$ to the receiving point at $P_2$ or thereabouts. This applies to the case where the flaw under consideration has a larger diameter than the scanning beam spot. In such a case, displacement may alternatively occur toward point $P_3$ or laterally. In the case of a mirror finished surface where the light level $A_1$ is shifted with respect to the point $P_1$, the fact that the output current of the regularly-reflected light receiving element is considerably reduced, may permit detection of such a defect in shape larger in diameter than the beam spot; however, in the case of a dull finished surface, it will be seen from FIG. 3 of the drawing that the light level $B_1$ is already so low that variations in the output current of the light receiving element resulting from a shift of the light level from $B_1$ to $B_2$ represents such a small difference in detected light that such variations are not easily discriminated from the variations in light receiving level due to the surface finish. Further, the output current of the light receiving element also may be reduced by other defects in the surface of the object or defects of the element.

However, it will be noted from diagram (b) of FIG. 3 that a significant difference in light level is detected at points $P_2$ and $P_3$ when the light level is shifted from $B_1$ to $B_2$, so that defects in shape can be detected by detecting the difference in output current of the light receiving elements $Ph_2$ and $Ph_3$ disposed at point $P_2$ and $P_3$, that is, $|I_2 - I_3|$. In other words, in the case of a defect in shape having a diameter larger than that of the light beam spot, an increased amount of light received by any of the irregularly-reflected light receiving elements $Ph_2$, $Ph_3$, ... in the neighborhood of the regularly-reflected light receiving element $Ph_1$ results in a reduced amount of light received by an irregularly-reflected light receiving element disposed symmetric with respect thereto. Thus, in the event that there is no abnormality, the difference between the output currents of the irregularly-reflected light receiving elements, such as elements $Ph_2$ and $Ph_3$, which are symmetric with each other is zero; whereas, there is a difference therebetween if there is a defect in shape, thus making it possible to easily detect such a defect in shape.

Generally, the scanning beam has a spot diameter of about 1mm to 5mm and in diagram (c) of FIG. 3 the curve $B_3$ shows the distribution of the amount of light received by the light receiving elements from a dull surface when there is a scratch or other defect on the surface in the form of an unevenness having a diameter not larger than that of the scanning light beam spot. Light reflected on such a small defect is generally scattered substantially equally right and left or upward and downward. In the case under consideration, the amount of light received is reduced at point $P_1$, while light received at points $P_2$ and $P_3$ is increased by substantially the same amount. The difference between the output current of the light receiving elements $Ph_2$ and $Ph_3$, that is, $|I_2 - I_3|$ is almost zero. For this reason, if the difference between the output currents at points $P_2$ and $P_3$ is determined to be almost zero in coincidence with a separate detection of an increase in the output of the irregularly-reflected light receiving elements $Ph_2$ and/or $Ph_3$, it indicates the presence of a scratch or other defect in the form of unevenness on the surface of the inspected object.

The diagram (d) in FIG. 3 shows the distribution of light received from a defect such as a smear, stain, or other color spot. Generally, the curve representing the distribution of received light due to increased light absorption by a defect is similar to, but uniformly lower in level than, the normal light distribution curve. Such a defect in the form of a color spot may be discriminated when it is found that the total output of the light-receiving elements $Ph_1$, $Ph_2$, $Ph_3$ and so forth, or the output of the element $Ph_1$ in the case of mirror finished surface, has decreased and that the difference between the outputs of the symmetric elements $Ph_2$ and $Ph_3$, that is, $|I_2 - I_3|$ is substantially zero.

Even though the above description involves a pair of irregularly-reflected light receiving elements arranged vertically upwardly and downwardly of the regularly reflected light receiving element, as shown in FIG. 2, accurate flaw detection also may be achieved by following the same processes through use of similar irregularly-reflected light receiving elements ($Ph_4$, $Ph_5$, ...) positioned horizontally or at different angles. Also, an optimum spaced relationship between the light-receiving elements depends on the diameter of expansion of the beam spot, the size of the apparatus or the light receiving elements and the distance between the reflection and receiving points, all of which are factors contributing to variations in the amount of received light shown in FIG. 3.

The manner in which the above-mentioned various types of defects are detected discriminatively will be described below with reference to the circuit shown in the block diagram of FIG. 4.

Symbols $P_1$ to $P_5$ represent points at which the light receiving elements $Ph_1$ to $Ph_5$ are positioned, which elements may be arranged vertically horizontally or at other angles symmetrically with respect to the regularly-reflected light receiving element $Ph_1$. Comparators $CP_1$ to $CP_6$ compare the analog signals or output current received from the light receiving elements with reference levels being set for each comparator so as to produce a signal with the logic level or "1" when the analog signal exceeds a certain threshold voltage. Symbols $S_1$ to $S_5$ and $S_2'$ to $S_5'$ represent switches for selectively switching a given one or plurality of light receiving elements depending on the state of the surface finish or the kind of defects to be inspected. An output is produced at the terminal 1 when a defect in shape larger in diameter than the beam spot is discovered; an output is produced at the terminal 2 in the presence of a color spot defect; and an output is produced at the terminal 3 in the presence of a scratch or other uneveness smaller in diameter than the beam spot.

Figure 4:
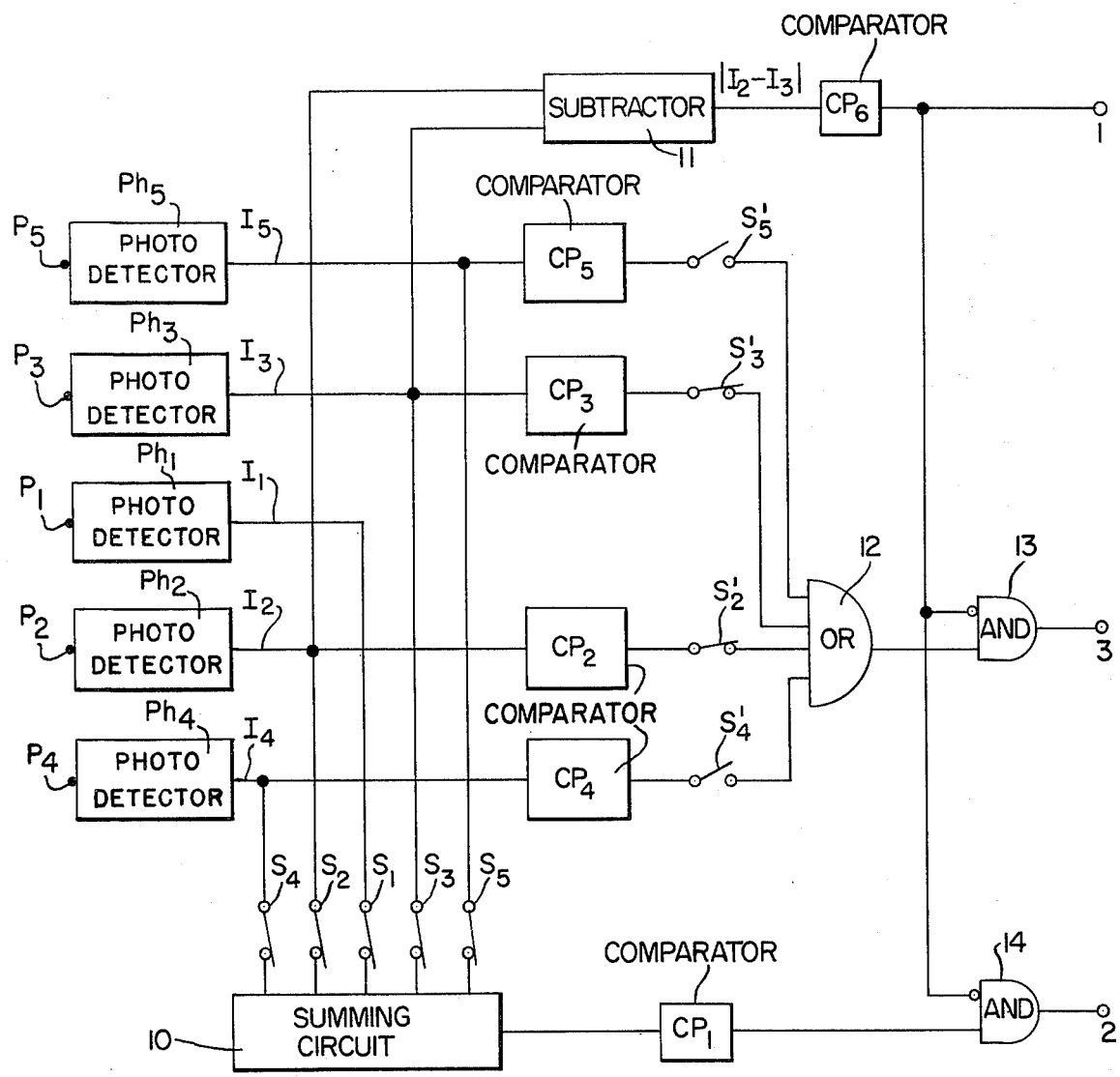
FIG. 4 is a block diagram showing a circuit for discriminatively detecting various types of defects according to the present invention.
Figure 5:
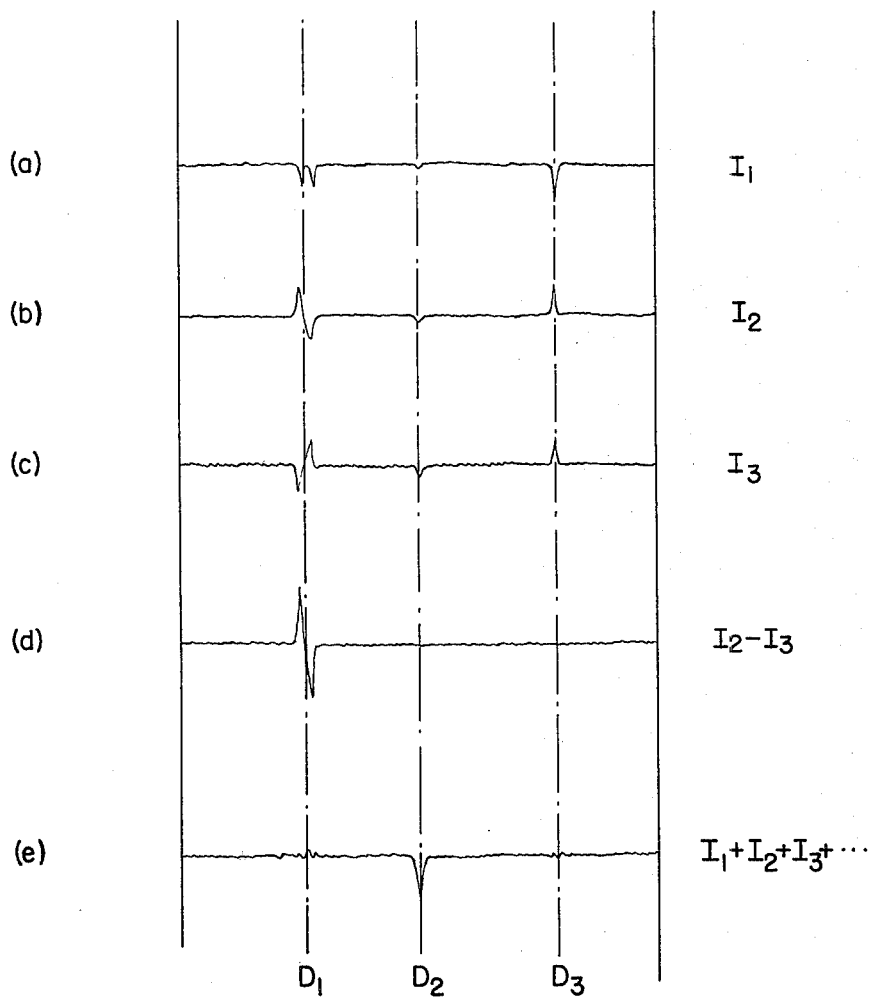
FIG. 5 is a diagram showing waveforms produced from various parts of the circuit of FIG. 4.

The diagram of FIG. 5 shows waveforms produced at various sections of the circuit of FIG. 4 during the period of one transverse scanning of the surface of the object to be inspected. In the drawing, waveform (a) represents the output current $I_1$ produced from the regularly-reflected light receiving element $Ph_1$; waveform (b) represents the output current $I_2$ produced from the light receiving element $Ph_2$; waveform (c) represents the output current $I_3$ produced from the light receiving element $Ph_3$; waveform (d) represents the output $I_2 - I_3$ produced from the subtractor 11, and waveform (e) represents the output of synthetizer 10 which serves to sum the outputs of the detectors to produce a signal in the form of $I_1 + I_2 + I_3 + \ldots$. On vertical line $D_1$ for each waveform there is shown the effect on the signal of a defect in shape larger in diameter than the beam spot. On line $D_2$ a color spot defect affects the signal, and on line $D_3$ an uneveness defect including a scratch affects the signal.

First of all, a description will be made of the operation for detecting a defect in shape. The difference between the output currents $I_2$ and $I_3$ of the light receiving elements $Ph_2$ and $Ph_3$ positioned to be symmetric with respect to the light receiving element $Ph_1$ is detected by the subtractor 11. When the difference $|I_2 - I_3|$ exceeds a certain level set by the comparator $CP_6$, an output signal is produced by the comparator at terminal 1. In the process, the absolute input value $|I_1 - I_3|$ may be obtained either by extracting the absolute value of the result of the subtraction $I_2 - I_3$ or by applying the result of the subtraction $I_2 - I_3$ and by defining the upper and lower limits of signal variations by a window comparator. In any event, it will be obvious from FIG. 5 that output variations of the symmetrically disposed light receiving elements $Ph_2$ and $Ph_3$ are in opposite phase and therefore the other defects are offset in the direction of $|I_2 - I_3|$, with the result that only the defect in shape is emphasized to facilitate the direction thereof.

Secondly, the operation for discriminating and detecting a color spot defect, such as a smear or stain, will be explained. The switches $S_1$ to $S_5$, or only $S_1$ in the case of mirror finished surface, is closed and the outputs $I_1, I_2, \ldots$ are added by the synthetizer 10. The reference level of the comparator $CP_1$ is set in such a manner that a defect signal is applied to AND gate 14 and produced at the terminal 2 when the output in the form of $I_1 + I_2 + I_3 + \ldots$ of the synthetizer is reduced below the highest level associated with the absence of any defect.

The composite output signal $(I_1 + I_2 + I_3 \ldots)$ from comparator $CP_1$ is reduced most in the case of a color spot defect, as seen in diagram (d) in FIG. 3, whereas it undergoes little change as it is offset in the case of a defect in shape or other small uneveness, as shown by waveform (e) of FIG. 5, the last color spot detect being inhibited by the defect-in-shape output from comparator $CP_6$ at the input to AND gate 14. In other words, a color spot defect signal is produced from the output of AND gate 14 at the terminal 2 when the composite output is reduced and the output $I_2 - I_3$ is zero.

Finally, explanation will be made of the operation for discriminating and detecting other small uneveness defects, such as scratches. First of all, at least one of the irregularly-reflected light receiving elements $Ph_2$, $Ph_3$, ..., other than the light receiving element $Ph_1$, are selected by the switches $S_2'$ to $S_5'$ and the reference levels of the comparators $CP_2$ to $CP_5$ are set in such a manner as to produce a defect output when the output current $I_2$ to $I_5$ of the light receiving elements is higher than in the absence of a defect.

As a result, a defect output is produced from the OR circuit 12 when any of the selected outputs of the light receiving elements $Ph_2$, $Ph_3$, $Ph_4$ and so on are increased. In view of the fact that the above-mentioned defect output may be also produced in the case of defect in shape, discrimination therefrom is made by inhibiting the last small uneveness defect output by use of a defect-in-shape output from comparator $CP_6$ to the input of AND gate 13. In other words, when any of the outputs $I_2$, $I_3$, $I_4$ and so on exceeds a certain level and the equation $|I_2 - I_3| \doteq 0$ is satisfied, a small uneveness defect is detected discriminatively from the output of AND gate 13 at terminal 3.

It will be understood from the above explanation that according to the present invention almost all the defects that may exist on the surface of a running object can be detected without fail and also it is possible to inspect successfully the dull surface of the object.

What is claimed is:

1. A method of inspecting the surface of a running object comprising the steps of scanning the surface of a running object with a spot light source through an optical scanning means, condensing said light reflected on said surface of said running object, detecting a regularly reflected component of said light at the point of said condensation, simultaneously detecting irregularly reflected light components at a plurality of predetermined positions in the vicinity of said condensation point, summing the detected light components derived at said respective positions, comparing said sum with a predetermined reference value, and producing an output representing a defect when said total deviates from said reference value, thereby making it possible to detect said defect discriminatively without being affected by the manner in which said surface of said object is finished.

2. A method of inspecting the surface of a running object comprising the steps of scanning the surface of a running object with a spot light source, condensing said light reflected on said surface of said running object, detecting a regularly reflected component of said light at the point of said condensation, simultaneously detecting irregularly reflected light components at a plurality of predetermined positions in the vicinity of said condensation point, comparing a predetermined reference value with the absolute value of the difference between the output current of at least two of said irregularly reflected light receiving photoelectric converter elements disposed punctually symmetric with respect to said condensation position, and producing an output representing a defect when said difference exceeds said reference value, thereby making it possible to detect a defect discriminatively.

3. A method of inspecting the surface of a running object comprising the steps of scanning the surface of a running object with a spot light source, condensing said light reflectd on said surface of said running object, detecting a regularly reflected component of said light at the point of said condensation, simultaneously detecting irregularly reflected light components at a plurality of predetermined positions in the vicinity of said condensation point, comparing individual components of said irregularly reflected light with a predetermined reference value, and producing a signal representing a defect when an individual value of a light component exceeds said reference value without any change in the absolute value of the light components at least at two of said irregularly reflected light positions which are symmetric with respect to said condensation point, thereby making it possible to detect a defect discriminatively.

4. An apparatus for inspecting the surface of a running object for defects comprising
    means for continuously scanning a spot of light over the surface of said running object,
    means for condensing the light reflected from said surface as a result of such scanning,
    a first detector positioned at a point at which regularly reflected light will be projected by said condensing means,
    a plurality of second detectors disposed at predetermined positions in the vicinity of said first detector so as to detect irregularly reflected light, and
    control means responsive to the outputs from said first and second detectors for generating a flaw indicating signal,
    said control means including first means for detecting a difference between the outputs of at least two of said second detectors which are disposed symmetrically on diametrically opposite sides of said first detector and second means responsive to an output of said first means in excess of a predetermined threshold for generating a first flaw indicating signal.

5. An apparatus as defined in claim 4 wherein said first means comprises a subtractor receiving the output of two of said second detectors.

6. An apparatus as defined in claim 5 wherein said second means comprises a first comparator.

7. An apparatus as defined in claim 4 wherein said control means further includes third means for individually comparing the outputs of at least one of said second detectors with a predetermined threshold, fourth means for providing an output in response to the detection by said third means of the output of said second detector exceeding said predetermined threshold, and fifth means responsive to the output from said fourth means and no output from said second means for generating a second flaw indicating signal.

8. An apparatus as defined in claim 7 wherein said third means comprises a second comparator connected to the output of said second detector.

9. An apparatus as defined in claim 7 wherein said third means comprises a plurality of second comparators each connected to an output of a respective one of said second detectors.

10. An apparatus as defined in claim 9 wherein said fourth means comprises an OR gate having inputs connected to the outputs of said second detectors.

11. An apparatus as defined in claim 10 wherein said fifth means comprises an AND gate having one input connected to the output of said OR gate and an inhibiting input connected to the output of said second means.

12. An apparatus as defined in claim 7 wherein said control means further comprises sixth means for adding the outputs of at least two detectors of the group of first and second detectors, seventh means for comparing the output of said sixth means with a predetermined reference value, and eighth means responsive to the output of said seventh means and no output from said second means for generating a third flaw indicating signal.

13. An apparatus as defined in claim 12 wherein said sixth means comprises a signal summing circuit connected to the outputs of said first detector and a second detector.

14. An apparatus as defined in claim 12 wherein said sixth means comprises a signal summing circuit connected to the outputs of said first detector and at least two second detectors.

15. An apparatus as defined in claim 4 wherein said control means furter comprises third means for adding the outputs of at least two detectors of the group of first and second detectors, fourth means for comparing the output of said third means to a predetermined reference value, and fifth means responsive to the output of said fourth means and no output from said second means for generating a second flaw indicating signal.

16. An apparatus as defined in claim 15 wherein said third means comprises a signal summing circuit connected to the outputs of said first detector and a second detector.

17. An apparatus as defined in claim 15 wherein said third means comprises a signal summing circuit connected to the outputs of said first detector and at least two second detectors.

18. An apparatus for inspecting the surface of a running object for defects comprising
    means for continuously scanning a spot of light over the surface of said running object,
    means for condensing the light reflected from said surface as a result of such scanning.
    a first detector positioned at a point at which regularly reflected light will be projected by said condensing means,
    a plurality of second detectors disposed at predetermined positions in the vicinity of said first detector so as to detect irregularly reflected light, and
    control means responsive to the outputs from said first and second detectors for generating a flaw indicating signal,
    said control means including first means for comparing the output of at least one of said second detectors with a predetermined threshold and third means for generating a first flaw indicating signal in response to the detection by said first means of the output of said second detector exceeding said predetermined threshold.

19. An apparatus as defined in claim 18 wherein said first means comprises a plurality of first comparators each connected to an output of a respective one of said second detectors and said second means comprises an OR gate having inputs connected to the outputs of said first comparators.

20. An apparatus as defined in claim 19 wherein said control means further comprises third means for adding the outputs of at least two detectors of the group of first and second detectors, fourth means for comparing the output of said third means to a predetermined reference value, and fifth means responsive to the output of said fourth means and no output from said second means for generating a second flaw indicating signal.

21. An apparatus as defined in claim 20 wherein said third means comprises a signal summing circuit connected to the outputs of said first detector and a second detector.

22. An apparatus as defined in claim 20 wherein said third means comprises a signal summing circuit connected to the outputs of said first detector and at least two second detectors.

23. An apparatus for inspecting the surface of a running object for defects comprising
   means for continuously scanning a spot of light over the surface of said running object,
   means for condensing the light reflected from said surface as a result of such scanning,
   a first detector positioned at a point at which regularly reflected light will be projected by said condensing means,
   a plurality of second detectors disposed at predetermined positions in the vicinity of said first detector so as to detect irregularly reflected light, and
   control means responsive to the outputs from said first and second detectors for generating a flaw indicating signal,
   said control means including first means for adding the outputs of at least two detectors of the group of first and second detectors and second means for comparing the output of said first means to a predetermined reference value to generate a first flaw indicating signal when said output exceeds said reference value.

24. An apparatus as defined in claim 23 wherein said first means comprises a signal summing circuit connected to the outputs of said first detector and a second detector.

25. An apparatus as defined in claim 23 wherein said first means comprises a signal summing circuit connected to the outputs of said first detector and at least two second detectors.

26. An apparatus as defined in claim 23 wherein said control means further includes third means for detecting the difference between the outputs of at least two of said second detectors which are disposed symmetrically on diametrically opposite sides of said first detector and fourth means responsive to an output of said third means in excess of a predetermined threshold for generating a second flaw indicating signal.

27. An apparatus as defined in claim 26 further including fifth means for blocking said first flaw indicating signal in response to generation of said second flaw indicating signal.

28. An apparatus as defined in claim 27 wherein said fifth means comprises an AND gate.

* * * * *